United States Patent
Keller et al.

(10) Patent No.: US 10,807,304 B2
(45) Date of Patent: Oct. 20, 2020

(54) METHOD FOR IDENTIFYING LASER SINTERING POWDERS

(75) Inventors: Peter Keller, Krailling (DE); Thomas Mattes, Gilching (DE); Mandy Gersch, Ulm (DE); Johann Oberhofer, Stockdorf (DE); Anton Mayer, Gilching (DE)

(73) Assignee: EOS GmbH Electro Optical Systems, Krailling (DE)

( * ) Notice: Subject to any disclaimer, the term of this patent is extended or adjusted under 35 U.S.C. 154(b) by 588 days.

(21) Appl. No.: 12/592,162

(22) Filed: Nov. 19, 2009

(65) Prior Publication Data

US 2010/0140550 A1 Jun. 10, 2010

Related U.S. Application Data

(60) Provisional application No. 61/201,832, filed on Dec. 16, 2008.

(30) Foreign Application Priority Data

Nov. 20, 2008 (DE) .................. 10 2008 058 177

(51) Int. Cl.
*B29C 64/153* (2017.01)
*C09K 11/77* (2006.01)
(Continued)

(52) U.S. Cl.
CPC .......... *B29C 64/153* (2017.08); *B29C 39/025* (2013.01); *B29C 39/10* (2013.01);
(Continued)

(58) Field of Classification Search
USPC ................................. 252/301.4 R
See application file for complete search history.

(56) References Cited

U.S. PATENT DOCUMENTS 2,567,769 A * 9/1951 Head ................ 252/301.4 S
2,791,565 A * 5/1957 Runciman ............ 252/301.4 R
(Continued)

FOREIGN PATENT DOCUMENTS

CA 1 209 341 8/1986
CA 1 212 021 9/1986
(Continued)

OTHER PUBLICATIONS

Mixer Mill MM 200. Product Description [online]. Retsch, captured Aug. 12, 2007 via Internet Archive Wayback Machine (retrieved on Jun. 10, 2014). Retrieved from the Internet: http://web.archive.org/web/20071028184535/http://www.retsch.com/products/milling/ball-mills/mm-200/.*

(Continued)

*Primary Examiner* — Alexandra M Moore
*Assistant Examiner* — Ross J Christie
(74) *Attorney, Agent, or Firm* — Locke Lord LLP; Daniel J. Fiorello; Scott D. Wofsy

(57) ABSTRACT

A method is presented that makes possible the labelling of powders that can be applied as building material in a layer-additive manufacturing method such as a selective laser sintering method. To this effect the powder is mixed with at least one salt of a metal of the rare earths, wherein the salt has the property that it shows a luminescence when being irradiated with photons having a wavelength outside of the visible spectrum or with particle radiation. Thereby, parts that have been manufactured by means of the layer-additive manufacturing method can be identified with regard to the manufacturer, the place of manufacture or the manufacture date.

16 Claims, 1 Drawing Sheet

(51) Int. Cl.
  *B33Y 10/00* (2015.01)
  *B29C 39/02* (2006.01)
  *B29C 39/10* (2006.01)
  *B33Y 70/00* (2020.01)
  *B29L 11/00* (2006.01)
  *G01N 21/64* (2006.01)
  *G01N 33/38* (2006.01)

(52) U.S. Cl.
  CPC .............. *B33Y 10/00* (2014.12); *C09K 11/77* (2013.01); *B29L 2011/00* (2013.01); *B33Y 70/00* (2014.12); *G01N 21/6428* (2013.01); *G01N 33/38* (2013.01)

(56) References Cited

U.S. PATENT DOCUMENTS

| | | | |
|---|---|---|---|
| 2,946,656 A * | 7/1960 | Schreurs | 252/301.4 P |
| 3,440,092 A | 4/1969 | Best et al. | |
| 3,527,711 A * | 9/1970 | Barber et al. | 252/301.4 F |
| 3,570,056 A * | 3/1971 | Hall et al. | 425/86 |
| 3,684,730 A * | 8/1972 | Sobon | 252/301.4 R |
| 3,706,825 A * | 12/1972 | Hall et al. | 264/75 |
| 3,758,413 A * | 9/1973 | Peters | 252/301.4 F |
| 3,798,173 A * | 3/1974 | Nath et al. | 252/301.4 R |
| 4,572,803 A * | 2/1986 | Yamazoe et al. | 534/16 |
| 4,881,951 A | 11/1989 | Monroe et al. | |
| 4,897,300 A * | 1/1990 | Boehm | 428/195.1 |
| 5,210,411 A * | 5/1993 | Oshima et al. | 250/271 |
| 5,460,758 A | 10/1995 | Langer et al. | |
| 5,474,803 A * | 12/1995 | Kikuchi | 427/180 |
| 5,677,187 A * | 10/1997 | Anderson et al. | 436/27 |
| 5,753,274 A * | 5/1998 | Wilkening | B23K 26/34 264/255 |
| 6,165,609 A | 12/2000 | Curatolo | |
| 6,180,029 B1 | 1/2001 | Hampden-Smith et al. | 252/301.4 R |
| 6,211,526 B1 * | 4/2001 | Huston et al. | 250/484.4 |
| 6,322,728 B1 | 11/2001 | Brodkin et al. | |
| 6,375,874 B1 | 4/2002 | Russell et al. | |
| 6,387,339 B1 | 5/2002 | Kaneyoshi et al. | |
| 6,639,353 B1 | 10/2003 | Chadha | |
| 6,656,588 B1 | 12/2003 | Laine et al. | |
| 6,666,991 B1 * | 12/2003 | Atarashi et al. | 252/301.4 R |
| 6,672,343 B1 * | 1/2004 | Perret | B22F 3/004 141/12 |
| 6,824,714 B1 * | 11/2004 | Turck | B29C 67/0077 264/308 |
| 6,974,641 B1 | 12/2005 | Choy et al. | |
| 6,982,117 B2 * | 1/2006 | Smith | B32B 27/20 252/301.16 |
| 7,147,801 B2 * | 12/2006 | Kozee et al. | 252/301.16 |
| 7,157,854 B1 * | 1/2007 | Wedding | 313/582 |
| 7,279,234 B2 * | 10/2007 | Dean | 428/690 |
| 7,357,887 B2 * | 4/2008 | May | B29C 67/0088 156/62.2 |
| 7,443,903 B2 * | 10/2008 | Leonardo et al. | 372/97 |
| 7,449,238 B1 | 11/2008 | Villalobos et al. | |
| 2001/0036591 A1 * | 11/2001 | Schulz et al. | 430/270.1 |
| 2001/0042853 A1 * | 11/2001 | Hampden-Smith et al. | 252/301.4 R |
| 2002/0195747 A1 * | 12/2002 | Hull | B29C 41/12 264/401 |
| 2003/0118440 A1 * | 6/2003 | Zhao et al. | 415/118 |
| 2003/0126804 A1 | 7/2003 | Rosenflanz et al. | |
| 2003/0183807 A1 * | 10/2003 | Shankar et al. | 252/301.4 R |
| 2003/0194578 A1 * | 10/2003 | Tam | D01D 5/24 428/690 |
| 2004/0080256 A1 * | 4/2004 | Hampden-Smith et al. | 252/301.4 R |
| 2004/0137228 A1 | 7/2004 | Monsheimer et al. | |
| 2004/0156986 A1 * | 8/2004 | Yadav | 427/180 |
| 2004/0232583 A1 | 11/2004 | Monsheimer et al. | |
| 2005/0247912 A1 | 11/2005 | Akiyama et al. | |
| 2005/0277710 A1 | 12/2005 | Joyce et al. | |
| 2006/0073975 A1 * | 4/2006 | Thieme et al. | 505/125 |
| 2006/0105170 A1 * | 5/2006 | Dobson et al. | 252/301.4 R |
| 2006/0189113 A1 * | 8/2006 | Vanheusden et al. | 438/597 |
| 2007/0183918 A1 | 8/2007 | Monsheimer et al. | |
| 2007/0238056 A1 | 10/2007 | Baumann et al. | |
| 2007/0273951 A1 * | 11/2007 | Ribi | 359/237 |
| 2008/0057356 A1 * | 3/2008 | Shimomura et al. | 429/12 |
| 2008/0085828 A1 * | 4/2008 | Khan et al. | 501/152 |
| 2008/0131546 A1 * | 6/2008 | Perret et al. | 425/143 |
| 2008/0138604 A1 * | 6/2008 | Kenney | G06K 7/12 428/323 |
| 2008/0152889 A1 | 6/2008 | Brand | |
| 2008/0274028 A1 * | 11/2008 | Lin et al. | 252/301.4 R |
| 2008/0281019 A1 | 11/2008 | Giller et al. | |
| 2009/0118813 A1 * | 5/2009 | Scheuermann et al. | 623/1.15 |
| 2009/0166329 A1 | 7/2009 | Cors et al. | |

FOREIGN PATENT DOCUMENTS

| | | | |
|---|---|---|---|
| CN | 1235936 | 11/1999 | |
| CN | 1594163 | 3/2005 | |
| DE | 33 01 357 | 8/1984 | |
| DE | 199 62 953 | 7/2001 | |
| DE | 103 50 024 | 5/2005 | |
| DE | 10 2004 016 249 | 10/2005 | |
| EP | 0 555 947 | 8/1993 | |
| EP | 1110996 A1 | 6/2001 | |
| EP | 1 494 000 | 1/2005 | |
| EP | 1 431 352 | 4/2008 | |
| EP | 1 939 267 | 7/2008 | |
| EP | 1 942 172 | 7/2008 | |
| GB | 2455852 A1 | 5/1976 | |
| JP | EP 0555947 A1 * | 8/1993 | .............. B01J 2/006 |
| JP | 2007-113327 | 5/2007 | |
| WO | WO-90/03893 | 4/1990 | |
| WO | WO-98/28124 | 7/1998 | |
| WO | WO-98/46544 | 10/1998 | |
| WO | WO-2006/119759 | 11/2006 | |
| WO | WO-2007/024856 | 3/2007 | |
| WO | WO-2008/010044 | 1/2008 | |

OTHER PUBLICATIONS

Smith, Edgar Von. "Victor Von-Richter's Text-Book of Inorganic Chemistry Ed." vol. 1. (London) pp. 356-357.*

Dubey, Vikas; Kaur, Jagjeet; Agrawal, Sadhana. "Effect of Europium Doping Levels on Photoluminescence and Thermoluminescence of Strontium Yttrium Oxide Phosphor". Materials Science in Semiconducting Processing. vol. 31 (2015) pp. 27-37.*

Wise et al., "Chemical taggant detection and analysis by laser-induced breakdown spectroscopy", Applied Optics, Nov. 1, 2008, vol. 47, No. 31, Applied Optics, pp. G15-G20.

Extended European Search Report dated Dec. 27, 2011, issued on corresponding European Patent Application No. 11008886.1.

Exner et al., "Selective Laser Sintering—Fast Generation of Precise Parts—an Overview", Laser Technik Journal, vol. 5, No. 4, Sep. 2008.

\* cited by examiner

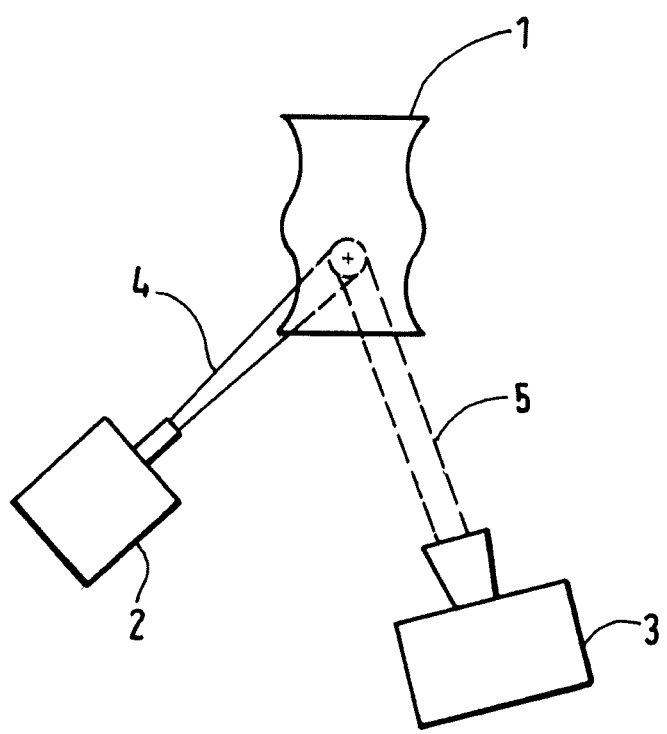

METHOD FOR IDENTIFYING LASER SINTERING POWDERS

The invention is directed to a method that allows to label the starting materials in powder form that are used in layer additive manufacturing methods with regard to their origin as well as to the use of such a labelled powder as raw material in a layer additive manufacturing method.

In the layer-wise manufacturing of objects from raw materials in powder form, for example by means of laser sintering, there is a problem that the raw materials in powder form can not be distinguished as to their appearance, though they are different powders. For instance, a flame resistant can optionally be added to a powder in order to achieve fire resistance of the object to be generated. Normally, such an additive does not change the appearance of the powder. In such a case it can usually be determined only by an elaborate analysis of the powder, whether a flame resistant was added.

Furthermore, it can also be important to determine for an already finished object and part, respectively, from which powder it has been manufactured. This can for example be an element of a failure analysis when the object does not have the desired characteristics. Even when the object is flawless, it can e.g. be desirable to know, sometimes after years, the supplier of the laser sintering powder that was used. Here, usually there shall not be the necessity to damage the object in an analysis, for example when a sample is taken.

An addition of colour pigments to the powder in order to label differing powder characteristics is unsuitable, because thereby the final colour of the object to be generated is affected, which in many cases is undesirable.

Therefore, the object of the invention is to provide a method that allows the identification of powders used in an additive layer manufacturing method, in particular a laser sintering method, and of parts manufactured from it, without altering the appearance of the powder and of the parts.

The object is achieved by a method for labelling a powder according to claim 1 and the use of such a powder according to claim 8 or 13.

Further developments according to the invention are described in the dependent claims.

By the method according to the invention it is in particular possible to exactly relate manufactured parts to a specific starting powder that was used. Thereby also after many years, when records have got lost or supply chains can no longer be traced back completely, it can be determined from which starting material of which producer the respective parts had been manufactured. In particular, it is also possible that the powder is not only labelled corresponding to a specific producer or to a specific production date, but that an indicator to the one, who has manufactured parts with this powder, is added. By the method according to the invention it is furthermore possible to carry out an identification even when only arbitrary small fragments of parts are available.

Further features and advantages of the invention will be described in the following based on an embodiment.

FIG. 1 shows an exemplary setup for illustrating a method for examining a labelled powder or parts manufactured thereof.

According to the invention for labelling a powder that is used in an additive layer manufacturing method such as a laser sintering method as building material in such a way that its properties or its origin from a specific producer are identifiable, the powder is mixed in a standard mixer with a marker powder. In order to avoid the situation that the characteristics of the starting powder are modified in a too strong way by the marker powder, it is advantageous when the fraction of the marker powder in the mixture does not exceed a certain percentage, e.g. 20 percent by weight. Of course, an even lower fraction, e.g. 10 percent by weight or even better between 0.1 and 10 percent by weight, is even more advantageous. However, when the fraction of the marker powder drops, also the probability to find still marker particles in small samples of the entire mixture goes down. With respect to a powder identification also for small amounts of powder, it is also important that the mixing is such complete that the final product is as homogenous as possible.

As the properties of the object to be manufactured shall not be changed by adding the marker substance that serves as identification means, the marker substance needs to be colourless or else needs to be added in such a low proportion that no change of the colour of the starting powder is observable. In order to be still able to identify a powder or a part according to the invention, a substance is chosen as marker, which shows a luminescence when being irradiated with light having a wavelength outside of the visible region such as infrared light or ultraviolet light. Then, for the identification the light that is emitted from the luminescent substance, has to be analysed for its wavelength and/or intensity. Thereby, solely based on presence of a luminescent emission it can be determined whether a marker had been added to the powder. If a luminescent emission is found for an irradiation, based on the irradiated (exciting) wavelength(s) and/or the emitted wavelength(s) it can be determined, which marker had been added.

Now a powder can be labelled by adding a tracer that emits a very specific wavelength or several characteristic wavelengths or a certain wavelength region. Of course it is also possible to use a tracer that shows a luminescence in various wavelength regions. In general an identification is possible via registering a very specific spectral distribution in the emitted light.

The labelled powder can be used as building material in any layer-additive manufacturing method for manufacturing three-dimensional objects, thus e.g. in a selective laser sintering or laser melting method or a selective electron beam and infrared, respectively, sintering or melting method, or else in a 3D printing method, in which a binder is spray-applied for solidifying the material. The mentioned methods are described among others in WO 90/03893 and U.S. Pat. No. 6,375,874 B1.

In FIG. 1 an exemplary setup for examining a part that has been manufactured by means of marked powder is shown. There, by means of a UV light source 2 UV light 4 is irradiated onto a laser-sintered part 1. A portion of the luminescent light 5, which has been excited by the irradiation, is detected by a detector 3.

For the excitation of the luminescence as an alternative to UV light also light having a different wavelength outside of the visible region, e.g. in the IR region, in a more preferable embodiment of the invention in the near infrared region (NIR), even more preferable between 900 nm and 1000 nm can be used. Furthermore, also an excitation of the luminescence by means of ionising radiation (particle radiation or X-ray radiation) is possible.

The detector for the analysis of the luminescent light can be a simple photodiode or else also a CCD or pixel sensor that detects the amount of light. In a most simple case the detection of the presence of a tracer happens by comparing the light emissions, with and without excitation light, of the powder or the finished product. The identification of the wavelengths of the luminescent light can e.g. be implemented by filter attachments in front of the detector, wherein each filter attachments shows a transmission only in a limited wavelength region. However, the use of other setups that provide a spectral decomposition (e.g. prisms, gratings, etc.) is possible. The spectral resolution can also be effected in the detector itself.

In order to determine the concentration of tracers in the powder or part for instance the amount of emitted luminescent light is measured without an attached filter and with an attached filter, respectively, wherein the filter shows a transmission only in the region of the luminescent spectrum. In this way the amount of luminescent light can be set in a relation to the total amount of light that is reflected from the powder or the part and is incident on the detector. A suitable calibration of the system provided, the amount of the added tracer can then be determined for the case that it is the amount of the added tracer that is used for coding the information.

In a modified embodiment two different tracers are added to the powder. The two different tracers show a light emission in different wavelength regions and/or have different exciting wavelengths. Then, a specific coding can be created by setting the proportion of the two added marker substances with respect to one another. The proportion is then determined in the analysis of the powder or part by setting the amounts of light that are emitted in both different wavelength regions in a relation to one another. In this way a corresponding encoding can be read. Of course, also more than two different tracers may be added. Furthermore, it is also possible to use a tracer that shows a luminescence in several wavelength regions.

Even if the emission regions of the two marker substances are overlapping with one another, the relative proportions of the two substances can be determined by using a spectrometer for analysing the luminescent radiation.

The described method can be applied to all possible powders, in particular to polymer powder, metal powder and sand-sintering powder. As for some of the mentioned powders very high temperatures occur during for example a sintering or melting process, with regard to a selection of the tracers there is the important requirement that the marker substances are not affected by the high temperatures that occur during the building process. It was found at a thermal resistance exists for the temperatures that normally occur in laser sintering methods, when using salts of the rare earths. These include e.g. oxides of the rare earths or oxysulfides or also fluorides, which are doped with minor additions of other elements that also originate from the group of the rare earths, in order to generate the desired luminescence.

Very advantageously, the marker substance can be admixed in such a way that the particles of the marker substance are embedded on the surface of the powder particles. In this way each individual powder particle can be marked. To this effect the marker substance and the powder particles are for example subjected to a method for the surface treatment of particles described in EP 0 555 947 A1. In the process the particles are fed into one of a plurality of impact chambers in communication with one another and equipped with a rotating disk having impact pins and also with an impingement rings, subjecting the mixture to an impact striking action, separating an air stream produced by that action from the powder mixture and discharging it continuously from the impact chamber, repeating the impact action while allowing the powder mixture to reside temporarily in the impact chamber, before causing the mixture to move, in succession, to the next chamber. Tests with such a commercial powder treatment machine NHS-1 of the company Nara showed that the duration of treatment for 8000 revolutions per minute has to be at least one minute (at room temperature).

Finally, it shall be pointed out that different marker substances or tracers can be recognized not only by the light that is emitted after an exitation, but also by the wavelength(s) that excites the luminescence.

What is claimed:

1. A method for labelling three-dimensional objects that have been manufactured from a building material in powder form by a layer-wise manufacturing process, the method having the following steps:
    mixing a powder that is used as a building material of an object made in said layer-wise manufacturing process with at least one salt of a metal of the rare earths, wherein the salt has the property that it shows a luminescence when being irradiated with photons having a wavelength outside of the visible spectrum or with particle radiation, and wherein the salt either is colorless or is added in such a low proportion that no change of the color of the powder is observable, wherein the salt encodes the powder, and
    manufacturing three-dimensional objects by said layer-wise manufacturing process, wherein the mixture in powder form that results from said mixing is used as the building material throughout the object in said layer-additive manufacturing process, wherein said layer-wise manufacturing process is an additive manufacturing process using selective laser sintering or selective laser melting or other high-energy beam technology for melting, fusing or sintering.

2. The method according to claim 1, further comprising in the mixing step adding at least two different salts of the rare earths, wherein each of the two different salts has a spectral emission during the luminescence of the salts that is different from that of the other salt.

3. The method according to claim 1, further comprising selecting the salt to be added as a marker, or the salts to be added as markers, depending on the identity of the powder producer, the identity of the applicant, the place of manufacture of the part that is manufactured by means of the layer-wise manufacturing process, or the powder composition.

4. The method according to claim 1, further comprising mixing the salt(s) with the powder by shear mixing.

5. The method according to claim 1, further comprising mixing the salt(s) with the powder by subjecting the powder particles to an impact striking action thereby providing an embed salt on the surface of the powder particles.

6. The method according to claim 1, further comprising adding a salt selected from the group consisting of doped oxides, oxysulfides and fluorides of the rare earths.

7. The method according to claim 4, further comprising adding a salt selected from the group consisting of doped oxides, oxysulfides and fluorides of the rare earths.

8. The method according to claim 5, further comprising adding a salt selected from the group consisting of doped oxides, oxysulfides and fluorides of the rare earths.

9. The method according to claim 6, further comprising adding a salt selected from the group consisting of yttrium oxide $Y_2O_3$, yttrium oxysulfide $Y_2O_2S$ or sodium yttrium fluoride $NaYF_4$, in each case doped with erbium or another element of the rare earths.

10. The method according to claim 1, further comprising providing information related to the powder composition, the powder producer, the powder user, the place of manufacture of the powder by mixing the powder with at least one salt of a metal of the rare earths to encode the powder.

11. The method according to claim 10, further comprising selecting the amount of the added salt to effect the encoding.

12. The method according to claim 10, further comprising selecting a specific salt or several specific salts to effect the encoding.

13. The method according to claim 10, further comprising selecting a specific combination of differing added salts to effect the encoding.

14. The method according to claim 10, further comprising selecting a specific relation between the amounts of the at least two added salts to effect the encoding.

15. A method for labelling three-dimensional objects to be manufactured from a building material in powder form by a layer-wise manufacturing process, the method comprising:

mixing a powder that is used as building material of an object in said layer-wise manufacturing process with at least one salt of a rare earth metal, wherein the salt has the property that it shows a luminescence when being irradiated with photons having a wavelength outside of the visible spectrum or with particle radiation, and wherein the salt either is colorless or is added in a such a low proportion that no change of the color of the powder is observable, wherein the salt encodes the powder, and providing the mixed powder as the building material for use in manufacturing the three- dimensional objects by a layer-wise manufacturing process, wherein the resulting objects will be marked by the at least one salt of a rare earth metal, wherein said layer-wise manufacturing process is an additive manufacturing process using selective laser sintering or selective laser melting or other high-energy beam technology for melting, fusing or sintering.

16. A method for making a powder for use in manufacturing labelled three-dimensional objects from a building material in powder form by a layer-wise manufacturing process, the method comprising:

making a mixed powder by mixing a powder that is used as building material of an object in said layer-wise manufacturing process with at least one salt of a rare earth metal, wherein the salt has the property that it shows a luminescence when irradiated with photons having a wavelength outside of the visible spectrum or with particle radiation, and wherein the salt either is colorless or is added in a such a low proportion that no change of the color of the powder is observable, wherein the salt encodes the powder, wherein three-dimensional objects manufactured using the mixed powder are marked by the at least one salt of a rare earth metal, wherein said layer-wise manufacturing process is an additive manufacturing process using selective laser sintering or selective laser melting or other high-energy beam technology for melting, fusing or sintering.

* * * * *